US00PP19525P2

(12) United States Plant Patent
Bunker

(10) Patent No.: US PP19,525 P2
(45) Date of Patent: Dec. 2, 2008

(54) *BRACTEANTHA* PLANT NAMED 'FLOBRAMAM'

(50) Latin Name: *Bracteantha bracteata*
Varietal Denomination: Flobramam

(75) Inventor: Kerry V. Bunker, Redland Bay (AU)

(73) Assignee: Floreta Intellectual Property Pty. Ltd. (AU)

( * ) Notice: Subject to any disclaimer, the term of this patent is extended or adjusted under 35 U.S.C. 154(b) by 0 days.

(21) Appl. No.: 11/879,610

(22) Filed: Jul. 18, 2007

(51) Int. Cl.
*A01H 5/00* (2006.01)

(52) U.S. Cl. ..... Plt./359

(58) Field of Classification Search ..... Plt./359
See application file for complete search history.

*Primary Examiner*—Kent L. Bell
*Assistant Examiner*—June Hwu

(57) ABSTRACT

A new and distinct cultivar of *Bracteantha bracteata* plant named 'Flobramam', characterized by its vibrant yellow inflorescences, compact plant habit, many inflorescences per plant, narrow leaf width, early flowering, and short peduncles.

1 Drawing Sheet

The present invention relates to a new and distinct cultivar of *Bracteantha* plant, botanically known as *Bracteantha bracteata*, and referred to by the variety denomination 'Flobramam'. The genus and species were formerly known as *Helichrysum bracteatum*, and *Bracteantha bracteata* is synonymous with the more recent botanical designation *Xerochrysum bracteatum*. The species is also known by the common names strawflower, paper daisy, and everlasting daisy.

The new cultivar is the product of a planned breeding program carried out by the inventor in Redland Bay, Queensland, Australia during November 2001. The objectives of the breeding program were to create new cultivars having a compact bushy habit, narrow leaves, and many inflorescences which have a range of colors and are held above the foliage on short peduncles.

The female or seed parent was unpatented Proprietary Selection 99-268. The characteristics of the female parent are upright plant habit; tall plant size; the leaves are broad in width; late flowering; involucral bracts which are few in number, curve upward giving a cupped shape to the inflorescence head, and are yellow in color; and short peduncles.

The male or pollen parent is unknown since the pollination was performed in isolation using native insects. Possible male parents are unpatented Proprietary Selection 99-420 and unpatented Proprietary Selection 99-579. The characteristics of Proprietary Selection 99-420 are upright plant habit; tall plant size; broad leaf width; large inflorescence size; many involucral bracts which are white in color, and long peduncles. The characteristics of Proprietary Selection 99-579 are upright plant habit; leaf width which is narrower than Selection 99-420 but larger than seed parent 99-268; many involucral bracts which are pale pink in color, and long peduncles.

The new cultivar was selected from the progeny of the described cross by the inventor in October 2002 in Redland Bay, Queensland, Australia. The first act of asexual reproduction of the new cultivar was accomplished when vegetative cuttings were made from the selection in October 2002 and grown in a controlled environment in Redland Bay, Queensland, Australia by or under the supervision of the inventor. Horticultural examination of controlled flowerings of successive plantings has shown that the unique combination of characteristics of the new cultivar are firmly fixed and are retained through successive generations of asexual reproduction.

The new cultivar has not been observed under all possible environmental conditions. The phenotype may vary significantly with variations in environment such as temperature, light intensity, fertilization levels, and day length without, however, any ariance in genotype. The following observations, measurements and comparisons describe plants grown in Redland Bay, Queensland, Australia under normal commercial growing conditions. The age of the plant described is 16 weeks.

SUMMARY OF THE INVENTION

The following traits have been repeatedly observed and have been determined to be basic characteristics of the new cultivar, which in combination distinguish the new cultivar as being new and distinct:

1. Vibrant yellow inflorescences.
2. Compact plant habit.
3. Many inflorescences per plant.
4. Narrow leaf width.
5. Early flowering.
6. Short peduncles.

The new cultivar differs from Proprietary Selections 99-420 and 99-579 by its vibrant yellow flowers, compact plant habit, narrow leaf width, earlier flowering, more flowers per plant, and short peduncle length. The new cultivar differs from its female parent by its compact plant habit, narrow leaf width, earlier flowering, and more flowers per bush.

Of the many commercial cultivars known to the present inventor, the most similar in comparison to the new cultivar is the cultivar 'Redbragol', disclosed in U.S. Plant Pat. No. 12,988. Based on comparative testing conducted in Redland Bay, Queensland, Australia, plants of the new cultivar differ from plants of the comparison cultivar in the characteristics as described in Table 1:

TABLE 1

| Trait | 'FLOBRAMAM' | 'REDBRAGOL' |
|---|---|---|
| Internode length | short | long |
| Leaf width | narrow | broad |
| Inflorescence number | many | few |
| Inflorescence size | medium | large |
| Plant height | medium | tall |
| Flowering time | early | late |

BRIEF DESCRIPTION OF THE PHOTOGRAPHS

The top photograph shows an overall view of a typical flowering plant of the new cultivar grown in a 14 cm container for about 10 weeks.

The bottom photograph shows a close up view of a typical inflorescence of the new cultivar.

The colors in the photographs show the colors as true as is reasonably possible with colored reproductions of this type. If any differences exist between the photographic color and the color values described below, the values in the detailed description are accurate.

DETAILED BOTANICAL DESCRIPTION

In the following description color references are made to The Royal Horticultural Society Colour Chart. The values are based on plant materal 16 weeks old grown in Redland Bay, Queensland, Australia, and the values were taken on Jun. 15, 2007.

Botanical classification: *Bracteantha bracteata* 'Flobraele'.

*Seed parent.*—Proprietary Selection 99-268.

*Pollen parent.*—Unknown for reasons described.

Propagation:

*Type.*—Shoot top cutting.

*Time and temperature to initiate roots.*—Summer, about 21 to 28 days at 20 to 25 deg. C in the greenhouse; winter, about 28 to 35 days at 15 to 20 deg. C in the greenhouse.

*Rooting characteristics.*—Freely branching, fibrous, root density moderate, color pale brown.

Plant description:

*General appearance and form.*—Compact and bushy growth habit; upright, outwardly spreading and rounded plant form with dense foliage and inflorescences held above the foliage on short peduncles.

*Growth and branching habit.*—Freely branching with lateral branches forming at every node to produce a dense and bushy plant.

*Plant habit.*—Rounded, compact, highly branched, vigorous, plant height approximately 15 cm and plant width 35 cm of mature plant in 14 cm container.

*Plant height* (*soil level to top of plant*).—15 cm.

*Plant diameter.*—35 cm.

*Time to produce mature plant.*—After rooting, about 10 weeks are required to produce finished flowering plants in 14 cm. pots.

Branches:

*Number of branches per plant.*—79.

*Length.*—9 cm.

*Width.*—3.5 mm.

*Internode length*—About 1.5 cm.

*Orientation.*—Upright mounding.

*Texture.*—Slightly pubescent.

*Color.*—195 D.

Foliage description:

*Leaf shape.*—Linear elliptic.

*Arrangement.*—Alternate, single, sessile.

*Length.*—About 7.5 cm.

*Width.*—About 1.0 cm.

*Shape at apex.*—Acute.

*Shape at base.*—Sessile.

*Margin.*—Entire.

*Color of young foliage.*—Upper surface: 146B. Lower surface: 146C.

*Color of mature foliage:*Upper surface:146A. Lower surface:146B.

*Venation pattern.*—Pinnate.

*Venation color.*—Upper surface 146A, lower surface 146B.

*Leaf texture.*—Upper and lower surfaces are weakly pubescent.

Inflorescence description:

*Flower type.*—Single daisy-type composite inflorescence form. Involucral bracts and disc florets arranged acopetally on capitulum.

*Natural floweriing season.*—Natural flowering season is year-round in Redland Bay, Queensland, Australia.

*Quantity of inflorescences.*—At one time, more than 88 open flowers and buds per plant.

*Bud.*—Rate of opening (from showing color to fully open flower): 14 to 21 days. Length: About 22 mm. Diameter: About 11.5 mm. Shape: Broadly ovoid with acute apex. Color: 17C with 171 A streaks towards the apex.

*Inflorescence.*—Inflorescence depth: About 2.0 cm. Inflorescence diameter: About 3.8 cm. Fragrance: There is a strong sweet vanilla-like fragrance.

*Involucral bracts.*—Quantity per inflorescence: About 60 in multiple whorls. Length: 16.8 mm. Width: 4.0 mm. Shape: Ligulate, concave. Apex: Acute. Base: Truncate. Margin: Entire. Texture: Both surfaces, smooth, glabrous, papery, satiny. Color, upper surface when opening: 17C with 171A streaks towards the apex. Lower surface when opening: 17C with 171A streaks towards the apex. Upper surface, opened flower: 13A. Lower surface, opened flower: 12A.

*Disc florets.*—One whorl of female filiform florets surround the perimeter of the disc, the remainder of the disc is covered with bisexual disc forets.

*Bisexual disc florets.*—Shape: Tubular with five lobes. Length of individual floret: 7.0 mm. Width of individual floret: 1.0 mm. Quantity: 562. Diameter of mature disc: 14.5 mm. Color, immature discs: 23B. Color, mature disc: 23B. Peduncle: Strength: strong. Angle: upright, erect. Length: 2.0 cm. Color: 195D. Texture: slightly pubescent.

*Reproductive organs.*—Androecium: Present only on bisexual disc florets. Anther color: 23B. Anther shape: fused anther tube with five long thin linear anthers surrounding the style. Anther length: Minute. Pollen color: Yellow. Gynoecium: Present on both filiform and bisexual disc florets. Pistil length: About 8.5 mm. Stigma shape: Bi-parted. Stigma color: 23B. Style length: About 7.0 mm. Style color: 23B. Ovary color: No color to describe it because of its minute size.

Seed: No seed was observed on the specimens.

Disease/pest susceptibility: Plants of the new *Bracteantha* have not been observed to be resistant to pathogens or pests common to *Bracteantha*.

Temperature tolerance: Plants of the new cultivar have not been observed to cease flowering at the temperatures observed at Redland Bay, Queensland, Autralia.

Growth retardants: No growth retardants are required for commercial production and none were used on the plants observed in this description.

I claim:

1. The new and distinct cultivar of *Bracteantha* plant named 'Flobramam', as illustrated and described.

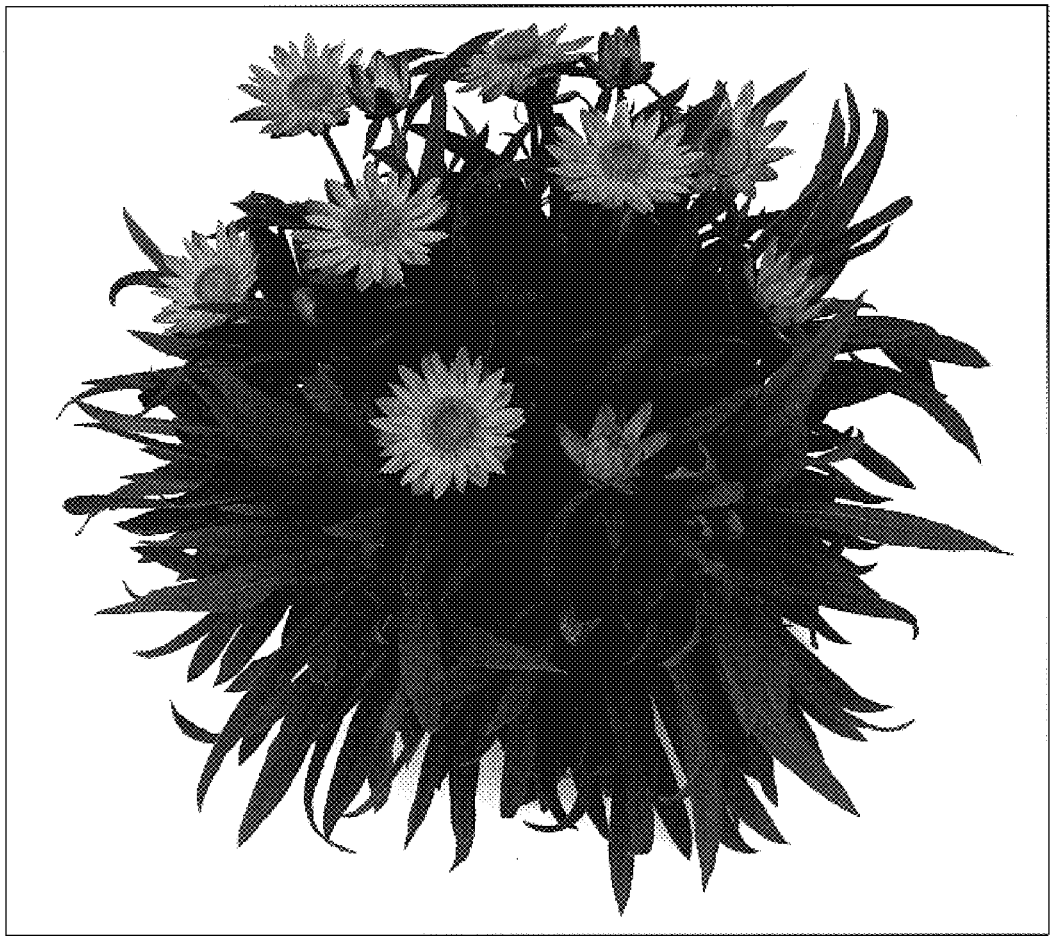
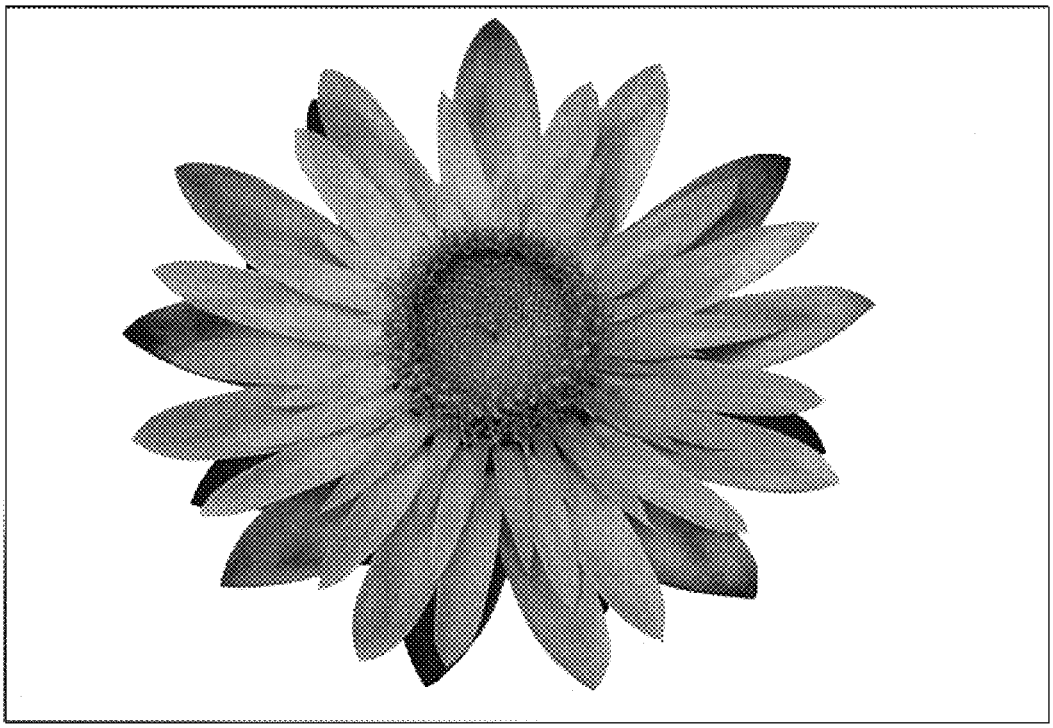

* * * * *